United States Patent
Vogel et al.

(10) Patent No.: US 7,319,153 B2
(45) Date of Patent: Jan. 15, 2008

(54) 6,13-BIS(THIENYL)PENTACENE COMPOUNDS

(75) Inventors: Dennis E. Vogel, Lake Elmo, MN (US); Kim M. Vogel, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 121 days.

(21) Appl. No.: 11/192,950

(22) Filed: Jul. 29, 2005

(65) Prior Publication Data

US 2007/0023748 A1    Feb. 1, 2007

(51) Int. Cl.
C07D 409/02    (2006.01)
(52) U.S. Cl. ............................. 549/4; 549/59
(58) Field of Classification Search .................. 549/4, 549/59
See application file for complete search history.

(56) References Cited

U.S. PATENT DOCUMENTS

| | | | |
|---|---|---|---|
| 5,347,144 | A | 9/1994 | Garnier et al. |
| 6,344,284 | B1 | 2/2002 | Chou |
| 6,361,885 | B1 | 3/2002 | Chou |
| 6,433,359 | B1 | 8/2002 | Kelley et al. |
| 6,617,609 | B2 | 9/2003 | Kelley et al. |
| 6,690,029 | B1 | 2/2004 | Anthony et al. |
| 2003/0105365 | A1 | 6/2003 | Smith et al. |
| 2003/0150384 | A1 | 8/2003 | Baude et al. |
| 2003/0151118 | A1 | 8/2003 | Baude et al. |
| 2003/0152691 | A1 | 8/2003 | Baude et al. |
| 2004/0222412 | A1 | 11/2004 | Bai et al. |

FOREIGN PATENT DOCUMENTS

| | | |
|---|---|---|
| JP | 2006/028054 | 2/2006 |
| WO | WO 01/45469 | 6/2001 |
| WO | WO 03/028125 | 4/2003 |

OTHER PUBLICATIONS

Vets et al. "Reduction versus Rearrangement of 6,13-Dihydro-6,13-diarylpenacene-6,13-diols Affording 6,13- and 13,13'-Substituted Pentacene Derivatives" Synlett, 2005, No. 2, pp. 217-222.*

Anthony et al., "A Road Map to Stable, Soluble, Easily Crystallized Pentacene Derivatives", Organic Letters, vol. 4, No. 1, 2002, pp. 15-18.

Anthony et al., "Functionalized Pentacene: Improved Electronic Properties from Control of Solid-State Order", J. Am. Chem. Soc., vol. 123, 2001, pp. 9482-9483.

Chan et al., "A Soluble Pentacene: Synthesis, EPR and Electrochemical Studies of 2,3,9,10-tetrakis(trimethylsilyl)pentacene", Chem. Commun. 2005, pp. 66-68.

Laquindanum et al., "Synthesis, Morphology, and Field-Effect Mobility of Anthradithiophenes" J. Am. Chem. Soc., vol. 120, 1998, pp. 664-672.

Payne et al., "Robust Soluble Pentacene Ethers" Organic Letters, vol. 6, No. 10, 2004, pp. 1609-1612.

Sheraw et al., "Spin-on Polymer Gate Dielectric For High Performance Organic Thin Film Transistors", Material Research Society Symposium Proceedings, vol. 558, 2000, pp. 403-408.

Sheraw et al., "Functionalized Pentacene Active Layer Organic Thin-Film Transistors", Adv. Mater., vol. 15, No. 23, 2003, pp. 2009-2011.

Yamada et al., "Photooxidation of the Evaporated Films of Polycyclic Aromatic Hydrocarbons Studied by X-Ray Photoelectron Spectroscopy" Bull. Chem. Soc., vol. 61, 1988, pp. 1057-1062.

N. Vets; M. Smets; W. Dehaen: "Reduction versus Rearrangement of 6, 13, Dihydro-6, 13-diarylpentacene-6, 13-diols affording 6, 13- and 13, 13'—Substituted Pentacene Derivatives" SYNLETT, No. 2, Dec. 2, 2004, pp. 217-222, XP002415894 compounds 3c-3d.

Q. Miao et al.: "Organization of Acenes with a Cruciform Assembly Motif" Journal of the American Chemical Society, vol. 128, No. 4, Jan. 10, 2006, pp. 1340-1345, XP002415895 Compound 2b.

* cited by examiner

*Primary Examiner*—Rebecca Anderson
*Assistant Examiner*—Joseph R. Kosack
(74) *Attorney, Agent, or Firm*—Jean A. Lown

(57) ABSTRACT

6,13-bis(thienyl)pentacene compounds are described that can be used as a semiconductor material. Semiconductor devices that contain the 6,13-bis(thienyl)pentacene compounds and methods of making such semiconductor devices are also described.

4 Claims, 2 Drawing Sheets

6,13-BIS(THIENYL)PENTACENE COMPOUNDS

TECHNICAL FIELD

The present invention provides 6,13-bis(thienyl)pentacene compounds. The invention also provides semiconductor devices and methods of making semiconductor devices that include a semiconductor layer that contains a 6,13-bis(thienyl)pentacene compound.

BACKGROUND

Traditionally, inorganic materials have dominated the semiconductor industry. For example, silicon arsenide and gallium arsenide have been used as semiconductor materials, silicon dioxide has been used as an insulator material, and metals such as aluminum and copper have been used as electrode materials. In recent years, however, there has been an increasing research effort aimed at using organic materials rather than the traditional inorganic materials in semiconductor devices. Among other benefits, the use of organic materials may enable lower cost manufacturing of electronic devices, may enable large area applications, and may enable the use of flexible circuit supports for display backplanes or integrated circuits.

A variety of organic semiconductor materials have been considered, the most common being fused aromatic ring compounds as exemplified by tetracene, pentacene, bis(acenyl)acetylene, and acene-thiophenes; oligomeric materials containing thiophene or fluorene units; and polymeric materials such as regioregular poly(3-alkylthiophene). At least some of these organic semiconductor materials have performance characteristics such as charge-carrier mobility, on/off current ratios, and sub-threshold voltages that are comparable or superior to those of amorphous silicon-based devices. These materials usually need to be vapor deposited since they are not very soluble in most solvents.

Because of its good electronic performance characteristics, pentacene is often the organic semiconductor of choice. However, pentacene can be difficult to synthesize and purify. Because of the limited solubility of pentacene in many common solvents, semiconductor layers containing pentacene typically cannot be formed using solvent-based deposition techniques. As an additional complication for solvent-based deposition techniques, pentacene tends to oxidize or undergo dimerization reactions in many solutions. Once deposited in a semiconductor layer, pentacene can oxidize over time. This can lead to reduced performance or complete failure of the semiconductor device that contains the oxidized pentacene.

SUMMARY

Compounds, semiconductor devices, and methods of making the semiconductor devices are described. More specifically, the semiconductor devices include a semiconductor layer that contains at least one 6,13-bis(thienyl)pentacene compound.

In one aspect, a 6,13-bis(thienyl)pentacene compound is described of Formula I.

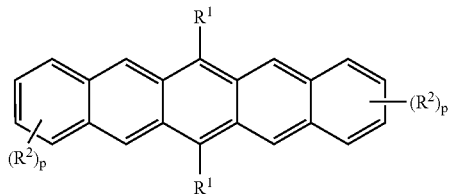

In Formula I, each $R^1$ is independently a thienyl group that is unsubstituted or substituted with an alkyl, alkenyl, alkynyl, aryl, halo, haloalkyl, trialkylsilyl, thienyl, or combinations thereof. Each $R^2$ in Formula I is independently an alkoxy, alkyl, alkenyl, alkynyl, amino, halo, haloalkyl, hydroxy, or two $R^2$ groups taken together form a fused ring. If $R^2$ is a fused ring, the fused ring has 5 to 7 ring members, is saturated or unsaturated, and is carbocyclic or heterocyclic. Each p in Formula I is independently an integer of 0 to 4.

In another aspect, semiconductor devices are described that include a semiconductor layer that contains a 6,13-bis(thienyl)pentacene compound of Formula I.

In yet another aspect, a method of preparing a semiconductor device is described. The method involves providing a semiconductor layer that contains a 6,13-bis(thienyl)pentacene compound of Formula I. The semiconductor layer can be formed using a vapor deposition technique or a solution deposition technique.

Some of the methods of preparing semiconductor devices are methods of preparing organic thin film transistors. One method of preparing an organic thin film transistor involves arranging multiple layers in the following order: a gate electrode; a gate dielectric layer; a semiconductor layer that includes a 6,13-bis(thienyl)pentacene compound of Formula I; and a layer having a source electrode and a drain electrode that are separated from each other, wherein the semiconductor layer contacts both the drain electrode and the source electrode.

Another method of preparing an organic thin film transistor involves arranging multiple layers in the following order: a gate electrode; a gate dielectric layer; a layer having a source electrode and a drain electrode that are separated from each other; and a semiconductor layer in contact with both the source electrode and the drain electrode. The semiconductor layer includes a 6,13-bis(thienyl)pentacene compound of Formula I.

As used herein, the terms "a", "an", and "the" are used interchangeably with "at least one" to mean one or more of the elements being described.

The term "alkyl" refers to a monovalent group that is a radical of an alkane, a saturated hydrocarbon. The alkyl can be linear, branched, cyclic, or combinations thereof and typically contains 1 to 30 carbon atoms. In some embodiments, the alkyl group contains 1 to 20, 1 to 14, 1 to 10, 4 to 10, 4 to 8, 1 to 8, 1 to 6, or 1 to 4 carbon atoms. Examples of alkyl groups include, but are not limited to, methyl, ethyl, n-propyl, isopropyl, n-butyl, tert-butyl, iso-butyl, n-pentyl, n-hexyl, cyclohexyl, n-octyl, n-heptyl, and ethylhexyl.

The term "alkenyl" refers to a monovalent group that is a radical of an alkene, a hydrocarbon with at least one carbon-carbon double bond. The alkenyl can be linear, branched, cyclic, or combinations thereof and typically contains 2 to 30 carbon atoms. In some embodiments, the alkenyl contains 2 to 20, 2 to 14, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkynyl" refers to a monovalent group that is a radical of an alkyne, a hydrocarbon with at least one carbon-carbon triple bond. The alkynyl can be linear, branched, cyclic, or combinations thereof and typically contains 2 to 30 carbon atoms. In some embodiments, the alkynyl contains 2 to 20, 2 to 14, 2 to 10, 4 to 10, 4 to 8, 2 to 8, 2 to 6, or 2 to 4 carbon atoms. Exemplary alkynyl groups include ethynyl, n-propynyl, and n-butynyl.

The term "alkoxy" refers to a monovalent group of formula —OR where R is an alkyl group. Examples include methoxy, ethoxy, propoxy, butoxy, and the like.

The term "amino" refers to a monovalent group of formula —N(R$^a$)$_2$ where each R$^a$ is independently hydrogen, alkyl, or aryl. Exemplary amino groups include, but are not limited to, —NH$_2$, —NHCH$_3$, —NH(C$_6$H$_5$), and —N(CH$_3$)$_2$.

The term "aryl" refers to a monovalent group that is a radical of an aromatic carbocyclic compound. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "carbocyclic" refers to a ring structure in which all the ring atoms are carbon.

The term "halo" refers to a halogen group (i.e., —F, —Cl, —Br, or —I).

The term "haloalkyl" refers to an alkyl substituted with at least one halo group.

The term "heterocyclic" refers to a ring structure in which the ring atoms include carbon and at least one heteroatom selected from oxygen, sulfur, or nitrogen.

The term "hydroxy" refers to a monovalent group of formula —OH.

When referring to a ring structure, the term "unsaturated" means that the ring includes at least one carbon-carbon double bond or carbon-carbon triple bond. Some unsaturated ring structures are aromatic or heteroaromatic.

When referring to a ring structure, the term "saturated" means that the ring structure contains no carbon-carbon double bonds or carbon-carbon triple bonds.

The term "thienyl" refers to a monovalent, heterocyclic group of formula —C$_4$H$_3$S.

The term "trialkylsilyl" refers to a monovalent group of formula —SiR$_3$ where each R is an alkyl.

The above summary of the present invention is not intended to describe each disclosed embodiment or every implementation of the present invention. The Figures, Detailed Description, and Examples that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
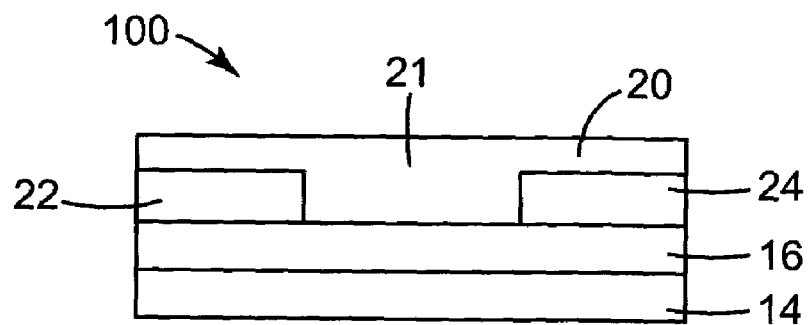
FIG. 1 is a schematic representation of a first exemplary thin film transistor.

The drawings are not meant to imply a certain thickness for any layer or to imply a certain relative thickness of various layers.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The present invention provides 6,13-bis(thienyl)pentacene compounds, semiconductor devices that contain a 6,13-bis(thienyl)pentacene compound, and methods of making semiconductor devices that contain a 6,13-bis(thienyl) pentacene compound. The 6,13-bis(thienyl)pentacene compounds have one or more of the following characteristics: improved solubility compared to pentacene, improved oxidative stability compared to pentacene, improved resistance to dimerization compared to pentacene, and mobilities comparable to other organic semiconductors when formed into a semiconductive layer.

Compounds

The 6,13-bis(thienyl)pentacene compounds are of Formula I.

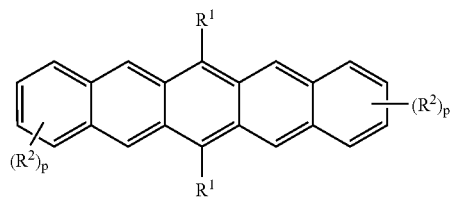

In Formula I, each R$^1$ is independently a thienyl group that is unsubstituted or substituted with an alkyl, alkenyl, alkynyl, aryl, halo, haloalkyl, trialkylsilyl, thienyl, or a combination thereof. Each R$^2$ in Formula I is independently an alkoxy, alkyl, alkenyl, alkynyl, amino, halo, haloalkyl, hydroxy, or two R$^2$ groups taken together form a fused ring. If R$^2$ is a fused ring, the fused ring has 5 to 7 ring members, is saturated or unsaturated, and is carbocyclic or heterocyclic. Each p in Formula I is independently an integer of 0 to 4.

R$^1$ is a thienyl group such as

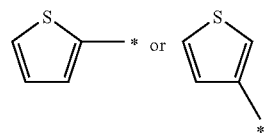

that is unsubstituted or substituted. The asterisk (*) indicates the carbon atom of the pentacene to which the thiophene is attached in Formula I. The two R$^1$ groups can be the same or different. In some embodiments, both of the R$^1$ groups are unsubstituted. In other embodiments, at least one R$^1$ group is substituted with one or more substituents. In still other embodiments, both R$^1$ groups are substituted with the same substituent or substituents. Substituents on R$^1$ can often improve the solubility of the compounds in various common solvents. The substituents can be an alkyl, alkenyl, alkynyl, aryl, halo, haloalkyl, trialkylsilyl, thienyl, or a combination thereof. When referring to the substituents of $R^1$, the term "combination thereof" means that $R^1$ can be substituted with more than one substituent (e.g., $R^1$ can be substituted with both an alkyl group such as methyl and an aryl such as phenyl) or that $R^1$ can be substituted with a substituent that is a combination of substituents (e.g., $R^1$ can be substituted with an aryl that is further substituted with an alkyl such as —$(C_6H_5)CH_3$ or $R^1$ can be substituted with an alkyl that is further substituted with an aryl such as —$CH_2(C_6H_5)$).

Suitable alkyl, alkenyl, and alkynyl substituents include, but are not limited to, those having up to 30, up to 20, up to 10, up to 6, or up to 4 carbon atoms. Exemplary alkyl substituents include methyl, ethyl, n-propyl, iso-propyl, n-butyl, iso-butyl, tert-butyl, n-pentyl, cyclopentyl, n-hexyl, cyclohexyl, and the like. Exemplary alkenyl groups include ethenyl, n-propenyl, n-butenyl, and the like. Exemplary alkynyl groups include ethynyl, n-propynyl, n-butynyl, and the like. Other substituents include thienyl groups (i.e., the substituted $R^1$ is a bithienyl group). Suitable halo substituents include fluoro, chloro, bromo, and iodo. Suitable haloalkyl groups include at least one halo and up to 30 carbon atoms, up to 20 carbon atoms, up to 10 carbon atoms, up to 6 carbon atoms, or up to 4 carbon atoms. Exemplary haloalkyl groups include perfluoroalkyl groups having 1 to 10 carbon atoms, 1 to 8 carbon atoms, 1 to 4 carbon atoms, or 1 to 3 carbon atoms. Such groups include $CF_3$, —$C_2F_5$, —$C_3F_7$, —$C_4F_9$, and the like. Suitable trialkylsilyl groups include, but are not limited to, those having alkyl groups with up to 6, up to 4, or up to 2 carbon atoms. Exemplary trialkylsilyl groups include trimethylsilyl, triethylsilyl, tri-isopropylsilyl, and the like. Suitable aryl group usually have up to 12 carbon atoms, up to 10 carbon atoms, up to 8 carbon atoms, or 6 carbon atoms. Exemplary aryl groups include phenyl, naphthyl, substituted phenyl (e.g., substituted with an alkyl, halo, haloalkyl, or trialkylsilyl), and the like.

Some $R^1$ groups are of formula

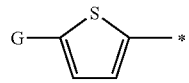

where G is hydrogen, alkyl, alkenyl, alkynyl, aryl, halo, haloalkyl, trialkylsilyl, thienyl, or a combination thereof. The $R^1$ group can be, for example, a thien-2-yl, 5-alkylthien-2-yl, 5-alkenylthien-2-yl, 5-alkynylthien-2-yl, 5-arylthien-2-yl, 5-halothien-2-yl, 5-haloalkylthien-2-yl, 5-trialkylsilylthien-2-yl, and bithien-2-yl. Specific examples of substituted $R^1$ groups include thien-2-yl, 5-methylthien-2-yl, 5-hexylthien-2-yl, 5-trimethylsilylthien-2-yl, and the like.

Each $R^2$ group in Formula I is an optional substituent on one of the outermost rings of the pentacene group. That is, $R^2$ is an optional substituent at the 1 to 4 position of the pentacene ring, at the 8 to 11 position of the pentacene group, or a combination thereof. These positions of the pentacene ring are shown in the following formula

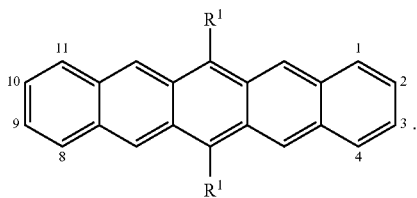

Each outmost ring can have no substituents or up to four substituents. In some exemplary compounds, there are no $R^2$ groups. In other exemplary compounds, both of the outermost rings of the pentacene group have one substituent. In still other exemplary compounds, both of the outermost rings of the pentacene group have more than one substituent or have a fused ring. The number and type of substituents on each of the outermost rings are often the same.

In some compounds, each $R^2$ is independently selected from an alkoxy, alkyl, alkenyl, alkynyl, amino, halo, haloalkyl, or hydroxy. Suitable alkyl, alkenyl, alkynyl, and alkoxy groups include, but are not limited to, those having up to 30 carbon atoms, up to 20 carbon atoms, up to 10 carbon atoms, up to 6 carbon atoms, or up to 4 carbon atoms. Exemplary alkyl substituents include methyl, ethyl, n-propyl, iso-propyl, n-butyl, iso-butyl, tert-butyl, n-pentyl, n-hexyl, cyclohexyl, and the like. Exemplary alkenyl groups include ethenyl, n-propenyl, n-butenyl, and the like. Exemplary alkynyl groups include ethynyl, n-propynyl, n-butynyl, and the like. Exemplary alkoxy groups include methoxy, ethoxy, propoxy, butoxy, and the like. Suitable haloalkyl groups include at least one halo and up to 30 carbon atoms, up to 20 carbon atoms, up to 10 carbon atoms, up to 6 carbon atoms, or up to 4 carbon atoms. Exemplary haloalkyl groups include perfluoroalkyl groups having 1 to 10 carbon atoms, 1 to 8 carbon atoms, 1 to 4 carbon atoms, or 1 to 3 carbon atoms. Such groups include, but are not limited to, —$CF_3$, —$C_2F_5$, —$C_3F_7$, —$C_4F_9$, and the like. Suitable amino groups can be of formula —$N(R^a)_2$ where each $R^a$ is independently hydrogen, alkyl, or aryl. Exemplary amino groups can be primary amino groups such as —$NH_2$, secondary amino groups such as —$NHCH_3$ or —$NH(C_6H_5)$, or tertiary amino groups such as —$N(CH_3)_2$.

In other compounds, two $R^2$ groups together form a fused ring to the pentacene group. If $R^2$ is a fused ring, the fused ring can have 5 to 7 ring members including those contributed by the pentacene group, can be saturated or unsaturated, and can be carbocyclic or heterocyclic. Suitable carbocyclic fused rings include, but are not limited to, cyclohexane, cyclopentane, and benzene. Suitable heterocyclic rings include, for example, those having a nitrogen heteroatom such as pyridine, pyridazine, pyrimidine, pyrazine, pyrrole, pyrazole, imidazole, triazole, and the like. Often, there is no fused ring or two fused rings (i.e., one fused ring attached to each of the outermost rings of the pentacene group). The fused rings can be attached to the pentacene group at a combination of the 1-2 positions, 2-3 positions, or 3-4 positions; at a combination of the 8-9 positions, 9-10 positions, 10-11 positions; or a combination thereof. For example, the fused rings can be attached to the 2-3 positions and to the 9-10 positions of the pentacene group.

In some embodiments, the 6,13-bis(thienyl)pentacene compounds are of Formula II:

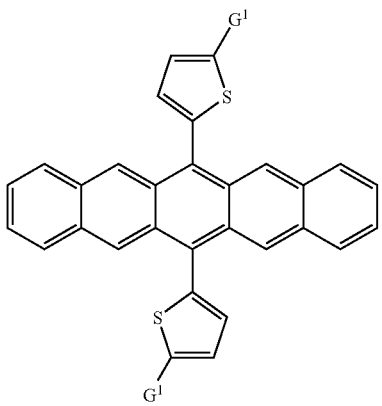

II

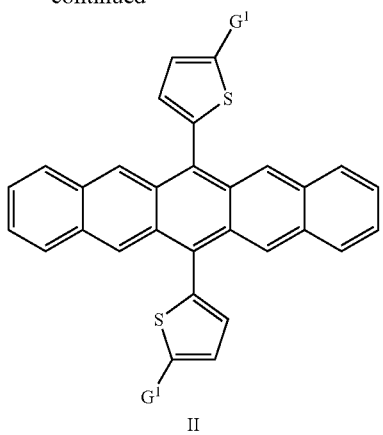

II where $G^1$ is hydrogen, alkyl, alkenyl, alkynyl, aryl, halo, haloalkyl, trialkylsilyl, thienyl, or a combination thereof. The compounds of Formula II do not have any $R^2$ groups (i.e., the variable p in Formula I is equal to 0). That is, there are no substituents on the outermost rings of the pentacene ring.

The 6,13-bis(thienyl)pentacene compounds of Formula II can be prepared as shown in Reaction Scheme A. A pentane-6,13-dione reactant can be prepared according to the procedure described by W. Ried et al., *Angewante Chemie*, 65, 601 (1953). According to this procedure, one equivalent cyclohexan-1,4-dione and two equivalents of o-phthalaldehyde are reacted in the presence of a 1M aqueous solution of sodium hydroxide. An intermediate diol is formed by reacting a thiophene with n-butyl lithium followed by the addition of the pentacene-6,13-dione. The intermediate diol can be treated with stannous chloride in aqueous hydrochloric acid to give the desired product.

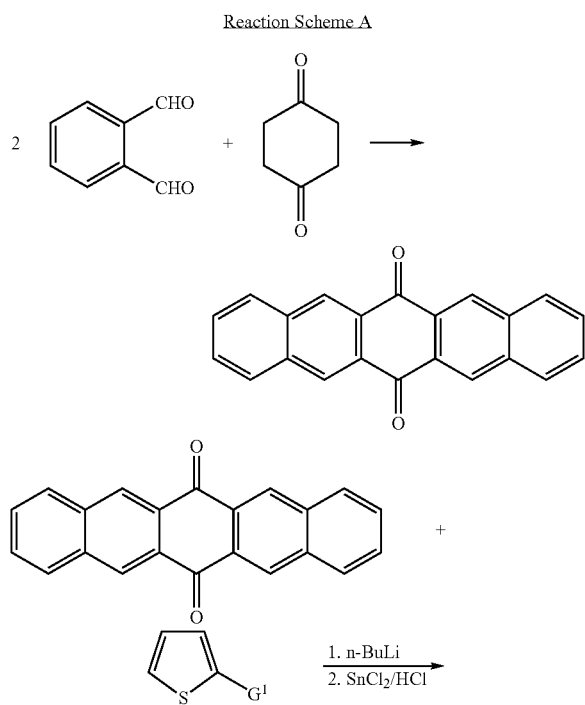

Reaction Scheme A

Substituents on the pentacene ring ($R^2$ groups as in Formula I) can be introduced by using a substituted o-phthalaldehyde. The substituted o-phthalaldehyde can be reacted with cyclohexane-1,4-dione as in Reaction Scheme A to produce a substituted pentacene-6,13-dione. Each o-phthalaldehyde can have 1 to 4 substituents $R^2$ groups on the ring in positions 3, 4, 5 or 6 corresponding to substitution in the pentacene-6,13-dione at positions 1, 2, 3, 4, 8, 9, 10 or 11. The $R^2$ groups are the same as those described above for Formula I.

The 6,13-bis(thienyl)pentacene compounds are soluble in a variety of common solvents such as, for example, hexane, dichloromethane, benzene, toluene, acetone, and tetrahydrofuran. The solubility is often at least 0.06 weight percent, at least 0.07 weight percent, at least 0.1 weight percent, at least 0.2 weight percent, at least 0.5 weight percent, at least 1.0 weight percent, at least 1.5 weight percent, at least 2.0 weight percent, at least 2.5 weight percent, at least 3.0 weight percent, at least 3.5 weight percent, at least 3.9 weight percent, or at least 4.0 weight percent. The weight percent is based on the weight of the solution. These solubility values are typically higher than for other known pentacene compounds such as those described, for example, in U.S. patent application Ser. No. 2003/0105365 A1 (Smith et al.).

The 6,13-bis(thienyl)pentacene compounds and the solutions containing these compounds are often resistant to oxidation in air. These compounds can be isolated in air and can be stored in solution for at least several hours without substantial degradation. The major impurity in the compounds is often an endoperoxide. The compounds can typically be stored in a solvent for at least 2, at least 3, or at least 4 hours with the increase in endoperoxide being less than 1 mole percent, less than 2 mole percent, or less than 3 mole percent. After about 120 hours (i.e., about 5 days), the increase in endoperoxide concentration in the solution is usually no greater than 20 mole percent, no greater than 18 mole percent, no greater than 17 mole percent, no greater than 15 mole percent, no greater than 12 mole percent, no greater than 10 mole percent, no greater than 8 mole percent, no greater than 4 mole percent.

Although the compounds tend to undergo some oxidation over time in solution, the resistance to oxidation is superior to many other known pentacene compounds. For example, Chan et al. in *Chem. Commun.*, 66-68 (2005) remarked that 2,3,9,10-tetrakis(trimethylsilyl)pentacene "is a highly air- and light-sensitive molecule, so that its isolation and purification must be carried out with a stringent exclusion of air and light using standard Schlenk techniques." Further, Laquindanum et al. in *J. Am. Chem. Soc.* 120, 664-672

(1998) stated that the small quantity of pentacene that could be extracted into refluxing 1,2-dichlorobenzene bleached in less than 5 minutes.

The 6,13-bis(thienyl)pentacene compounds tend to be resistant to dimerization when present in a solution. For example, these compounds can be stored for at least 120 hours (i.e., 5 days) without dimerization. The resistance to oxidation and dimerization are contributed, at least in part, to the presence of the thienyl groups.

Semiconductor Devices

Semiconductor devices are described that have a semiconductor layer that contains a 6,13-bis(thienyl)pentacene compound of Formula I. The semiconductor layer that contains a 6,13-bis(thienyl)pentacene compound can be included in any type of semiconductor device. Semiconductor devices have been described, for example, by S. M. Sze in *Physics of Semiconductor Devices*, $2^{nd}$ edition, John Wiley and Sons, New York (1981). Such devices include rectifiers, transistors (of which there are many types, including p-n-p, n-p-n, and thin-film transistors), photoconductors, current limiters, thermistors, p-n junctions, field-effect diodes, Schottky diodes, and the like.

Semiconductor devices can include components such as transistors, arrays of transistors, diodes, capacitors, embedded capacitors, and resistors that are used to form circuits. Semiconductor devices also can include arrays of circuits that perform an electronic function. Examples of these arrays, or integrated circuits, are inverters, oscillators, shift registers, and logic circuits. Applications of these semiconductor devices and arrays include radio frequency identification devices (RFIDs), smart cards, displays backplanes, sensors, memory devices, and the like.

Each semiconductor device contains a semiconductor layer with a 6,13-bis(thienyl)pentacene compound according to Formula I. The semiconductor layer can be combined with (e.g., adjacent to) a conductive layer, a dielectric layer, or a combination thereof to form the semiconductor device. For example, the semiconductor layer can be in contact with two electrodes such as a source electrode and a drain electrode that are separated from each other on a surface of the semiconductor layer. In another example, the semiconductor layer can be in contact with a dielectric layer. In yet another example, one surface of the semiconductor layer can be in contact with a conductive layer and the opposite surface of the semiconductor layer can be adjacent to a dielectric layer.

Some of the semiconductor devices are organic thin-film transistors. One embodiment of an organic thin-film transistor 100 is shown schematically in FIG. 1. The organic thin-film transistor (OTFT) 100 includes a gate electrode 14, a gate dielectric layer 16 disposed on the gate electrode 14, a source electrode 22, a drain electrode 24, and a semiconductor layer 20 that is in contact with both the source electrode 22 and the drain electrode 24. The source electrode 22 and the drain electrode 24 are separated from each other (i.e., the source electrode 22 does not contact the drain electrode 24) and are positioned adjacent to the dielectric layer 16. Both the source electrode 22 and the drain electrode 24 are in contact with the semiconducting layer such that a portion of the semiconductor layer is positioned between the source electrode and the drain electrode. The portion of the semiconductor layer that is positioned between the source electrode and the drain electrode is referred to as the channel 21. The channel is adjacent to the gate electrode 14 and the gate dielectric layer 16. Some semiconductor devices have an optional surface treatment layer between the gate dielectric layer 16 and the semiconductor layer 20.

Any given layer included the various electrodes in FIGS. 1 to 6 can include multiple layers of materials. Further, as used herein, the terms "disposed", "disposing", "deposited", "depositing", and "adjacent" do not preclude another layer between the mentioned layers. As used herein, these terms mean that a first layer is positioned near a second layer. The first layer often contacts the layer but another layer could be positioned between the first layer and the second layer.

An optional substrate can be included in the organic thin-film transistors. For example, the optional substrate 12 can be adjacent to the gate electrode 14 as shown schematically in FIG. 2 for the OTFT 200 or adjacent to the semiconductor layer 20 as shown schematically in FIG. 3 for the OTFT 300. The OTFT 300 can include an optional surface treatment layer between the substrate 12 and the semiconductor layer 20.

Figure 4:
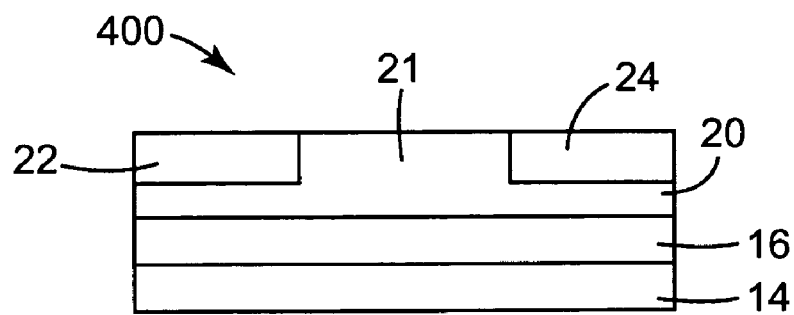
FIG. 4 is a schematic representation of a fourth exemplary thin film transistor.

Another embodiment of an organic thin-film transistor is shown schematically in FIG. 4. This organic thin-film transistor 400 includes a gate electrode 14, a gate dielectric layer 16 disposed on the gate electrode 14, a semiconductor layer 20, and a source electrode 22 and a drain electrode 24 disposed on the semiconductor layer 20. In this embodiment, the semiconductor layer 20 is between the gate dielectric layer 16 and both the source electrode 22 and the drain electrode 24. The source electrode 22 and the drain electrode 24 are separated from each other (i.e., the source electrode 22 does not contact the drain electrode 24). Both the source electrode 22 and the drain electrode 24 are in contact with the semiconducting layer such that a portion of the semiconductor layer is positioned between the source electrode and the drain electrode. The channel 21 is the portion of the semiconductor layer that is positioned between the source electrode 22 and the drain electrode 24. One or more optional surface treatment layers can be included in the semiconductor device. For example, an optional surface treatment layer can be included between the gate dielectric layer 16 and the semiconductor layer 20.

An optional substrate can be included in the organic thin-film transistors. For example, the optional substrate 12 can be in contact with the gate electrode 14 as shown schematically in FIG. 5 for the OTFT 500 or in contact with the semiconductor layer 20 as shown schematically in FIG. 6 for the OTFT 600. OTFT 600 can include an optional surface treatment layer between the substrate 12 and the semiconductor layer 20.

In operation of the semiconductor device configurations shown in FIGS. 1 to 6, voltage can be applied to the drain electrode 24. However, no charge (i.e., current) is passed to the source electrode 22 unless voltage is also applied to the gate electrode 14. That is, unless voltage is applied to the gate electrode 14, the channel 21 in the semiconductor layer 20 remains in a non-conductive state. Upon application of voltage to the gate electrode 14, the channel 21 becomes conductive and charge flows through the channel 21 from the source electrode 22 to the drain electrode 24.

A substrate 12 often supports the OTFT during manufacturing, testing, and/or use. Optionally, the substrate can provide an electrical function for the OTFT. For example, the backside of the substrate can provide electrical contact. Useful substrate materials include, but are not limited to, inorganic glasses, ceramic materials, polymeric materials, filled polymeric materials (e.g., fiber-reinforced polymeric materials), metals, paper, woven or non-woven cloth, coated or uncoated metallic foils, or a combination thereof. Suitable polymeric substrates include acrylics, epoxies, polyamides, polycarbonates, polyimides, polyketones, polynorbornenes, polyphenyleneoxides, poly(ethylene naphthalates), poly(ethylene terephthalates), poly(phenylene sulfides), poly(ether ether ketones) such as poly(oxy-1,4-phenyleneoxy-1,4-phenylenecarbonyl-1,4-phenylene), and the like.

The gate electrode 14 can include one or more layers of a conductive material. For example, the gate electrode can include a doped silicon material, a metal, an alloy, a conductive polymer, or a combination thereof. Suitable metals and alloys include, but are not limited to, aluminum, chromium, gold, silver, nickel, palladium, platinum, tantalum, titanium, or a combination thereof. Exemplary conductive polymers include, but are not limited to, polyaniline or poly(3,4-ethylenedioxythiophene)/poly(styrene sulfonate). In some organic thin film transistors, the same material can provide both the gate electrode function and the support function of the substrate. For example, doped silicon can function as both the gate electrode and as a substrate.

The gate dielectric layer 16 is disposed on the gate electrode 14. This gate dielectric layer 16 electrically insulates the gate electrode 14 from the balance of the OTFT device. Useful materials for the gate dielectric include, for example, an inorganic dielectric material, a polymeric dielectric material, or a combination thereof. The gate dielectric can be a single layer or multiple layers of suitable materials. Each layer in a single or multilayer dielectric can include one or more dielectric materials.

Exemplary inorganic dielectric materials include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, zinc sulfide, hafnium oxides, and the like. In addition, alloys, combinations, and multiple layers of these materials can be used for the gate dielectric layer 16.

Exemplary polymeric dielectric materials include polyimides, parylene C, crosslinked benzocyclobutene, cyanoethylpullulan, polyvinyl alcohol, and the like. See, for example, C. D. Sheraw et al., "Spin-on polymer gate dielectric for high performance organic thin film transistors", *Materials Research Society Symposium Proceedings*, vol. 558, pages 403-408 (2000), Materials Research Society, Warrendale, Pa., USA; and U.S. Pat. No. 5,347,144 (Garnier).

Other exemplary organic polymeric dielectrics include cyano-functional polymers such as cyano-functional styrenic copolymers as disclosed in U.S. Patent Publication 2004/0222412 A1 (Bai et al.), the disclosure of which is incorporated herein by reference. Some of these polymeric materials can be coated from solution, can be crosslinked, can be photo-patterned, can have high thermal stability (e.g., stable up to a temperature of about 250° C.), can have a low processing temperature (e.g., less than about 150° C. or less than about 100° C.), can be compatible with flexible substrates, or combinations thereof.

Exemplary cyano-functional polymers that can be used as organic dielectric materials include, but are not limited to, styrene maleic anhydride copolymers modified by adding a methacrylate functional group for crosslinking purposes and by attaching cyano-functional groups; the reaction product of bis(2-cyanoethyl)acrylamide with an acrylated polystyrene macromer; polymers formed from 4-vinylbenzylcyanide; polymers formed from 4-(2,2'-dicyanopropyl)styrene; polymers formed from 4-(1,1',2-tricyanoethyl)styrene; and polymers formed from 4-(bis-(cyanoethyl)aminoethyl)styrene; and a copolymer formed from 4-vinylbenzylcyanide and 4-vinylbenzylacrylate.

The organic thin film transistors can include an optional surface treatment layer disposed between the gate dielectric layer 16 and at least a portion of the organic semiconductor layer 20 or disposed between the substrate 12 and at least a portion of the organic semiconductor layer 20. In some embodiments, the optional surface treatment layer serves as an interface between the gate dielectric layer and the semiconductor layer or between the substrate and the semiconductor layer. The surface treatment layer can be a self-assembled monolayer or a polymeric material.

Suitable self-assembled monolayer surface treatment layers are disclosed, for example, in U.S. Pat. No. 6,433,359 B1 (Kelley et al.). Exemplary self-assembled monolayers can be formed from 1-phosphono-2-ethylhexane, 1-phosphono-2,4,4-trimethylpentane, 1-phosphono-3,5,5-trimethylhexane, 1-phosphonoctane, 1-phosphonohexane, 1-phosphonohexadecane, 1-phosphono-3,7,11,5-tetramethylhexadecane, and the like.

Useful polymers and copolymers for a surface treatment layer are usually non-polar, glassy solids at room temperature. The polymeric materials in this layer typically have glass transition temperature (Tg) measured in the bulk of at least 25° C., of at least 50° C., or of at least 100° C. Suitable polymeric surface treatment layers are described, for example, in U.S. Patent Application Publication 2003/0102471 A1 (Kelley et al.) and U.S. Pat. No. 6,617,609 (Kelley et al.)

Exemplary polymeric surface treatment layers can contain polystyrene, polyfluorene, polynorbornene, poly(1-hexene), poly(methyl methacrylate), poly(acenaphthylene), poly(vinylnaphthalene), poly(butadiene), and poly(vinyl acetate). Other exemplary polymeric surface treatment layers can contain polymers or copolymers derived from α-methylstyrene, 4-tert-butylstyrene, 2-methylstyrene, 3-methylstyrene, 4-methylstyrene, 4-(phosphonomethyl)styrene, divinyl benzene, and combinations thereof. Examples of still other useful polymeric materials for the surface treatment layer include poly(dimethylsiloxane), poly(dimethylsiloxane-co-diphenylsiloxane), poly(methylphenylsiloxane-co-diphenylsiloxane), poly(dimethylsiloxane-co-methylphenylsiloxane), and the like.

The surface treatment layer often has a maximum thickness less than 400 Angstroms (Å). For example, the surface treatment layer can be less than 200 Å, less than 100 Å, or less than 50 Å. The surface treatment layer generally has a thickness of at least about 5 Å, at least about 10 Å, or at least 20 Å. The thickness can be determined through known methods such as ellipsometry.

The source electrode 22 and drain electrode 24 can be metals, alloys, metallic compounds, conductive metal oxides, conductive ceramics, conductive dispersions, and conductive polymers, including, for example, gold, silver, nickel, chromium, barium, platinum, palladium, aluminum, calcium, titanium, indium tin oxide (ITO), fluorine tin oxide (FTO), antimony tin oxide (ATO), indium zinc oxide (IZO), poly(3,4-ethylenedioxythiophene)/poly(styrene sulfonate), polyaniline, other conducting polymers, alloys thereof, combinations thereof, and multiple layers thereof. Some of these materials are appropriate for use with n-type semiconductor materials and others are appropriate for use with p-type semiconductor materials, as is known in the art.

The thin film electrodes (e.g., the gate electrode, the source electrode, and the drain electrode) can be provided by any means known in the art such as physical vapor deposition (for example, thermal evaporation or sputtering), ink jet printing, or the like. The patterning of these electrodes can be accomplished by known methods such as shadow masking, additive photolithography, subtractive photolithography, printing, microcontact printing, and pattern coating.

Further, the semiconductor devices that contain the 6,13-bis(thienyl)pentacene compound tend to have performance characteristics such as charge-carrier mobility and current on/off ratio that are comparable to known organic semiconductor devices. For example, semiconductor devices can be prepared that have a charge mobility (e.g., hole mobility) of about $1.5 \times 10^{-2}$ cm$^2$/volt-sec, a threshold voltage of about −3 volts, a sub-threshold slope of about 1 to about 2 volts per decade, and on/off ratio greater than about $10^4$.

Methods of Preparing Semiconductor Devices

In another aspect, a method of preparing a semiconductor device is described. The method involves preparing a semiconductor layer that contains a 6,13-bis(thienyl)pentacene compound of Formula I. The semiconductor layer is usually formed using a vapor deposition process or a solution-based deposition process. Suitable methods of preparing semiconductor devices are further described by Peter Van Zant in *Microchip Fabrication*, Fourth Edition, McGraw-Hill, New York (2000).

In some exemplary methods of preparing a semiconductor device, the method involves providing a first layer selected from a dielectric layer or a conductive layer and disposing a semiconductor layer adjacent to the first layer. No specific order of preparing or providing is necessary; however, the semiconductor layer is often prepared on the surface of another layer such as the dielectric layer, the conductive layer, or a substrate. The conductive layer can include, for example, one or more electrodes such as a gate electrode or a layer that includes both the source electrode and the drain electrode.

Some of the methods of preparing semiconductor devices are methods of preparing organic thin film transistors. One method of preparing an organic thin film transistor involves arranging multiple layers in the following order: a gate electrode; a gate dielectric layer; a layer having a source electrode and a drain electrode that are separated from each other; and a semiconductor layer in contact with both the source electrode and the drain electrode. The semiconductor layer includes a 6,13-bis(thienyl)pentacene compound of Formula I. Exemplary organic thin film transistors according to this method are shown schematically in FIGS. 1 to 3.

The organic thin film transistor shown schematically in FIG. 1 can be prepared, for example, by providing a gate electrode 14; depositing a gate dielectric layer 16 adjacent to the gate electrode 14; positioning a source electrode 22 and a drain electrode 24 adjacent to the gate dielectric layer 16 such that the source electrode 22 and the drain electrode 24 are separated from each other; and forming a semiconductor layer 20 that is deposited on the source electrode 22, on the drain electrode 24, and in the area 21 between the source electrode 22 and the drain electrode 24. The semiconductor layer 20 contacts both the source electrode 22 and the drain electrode 24. The portion of the semiconductor layer that is positioned in the area between the source electrode and the drain electrode defines a channel.

Figure 2:
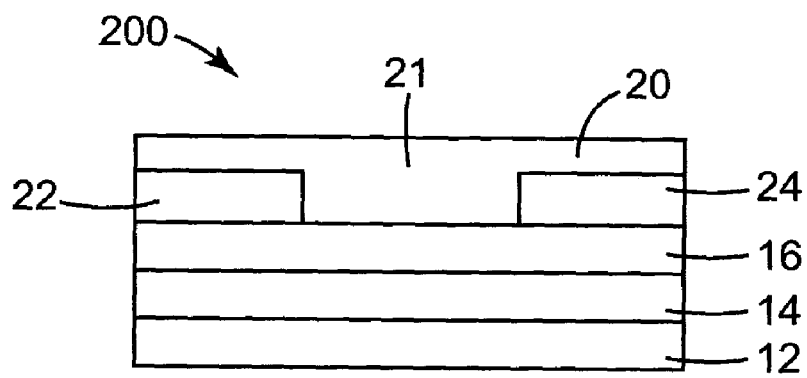
FIG. 2 is a schematic representation of a second exemplary thin film transistor.

The organic thin film transistor shown schematically in FIG. 2 can be prepared by providing a substrate 12; depositing a gate electrode 14 on the substrate 12; depositing a gate dielectric layer 16 adjacent to the gate electrode 14 such that the gate electrode 14 is positioned between the substrate 12 and the gate dielectric layer 16; positioning a source electrode 22 and a drain electrode 24 adjacent to the gate dielectric layer 16 such that the two electrodes are separated from each other; and forming a semiconductor layer 20 adjacent to the source electrode 22, the drain electrode 24, and in the area 21 between the source electrode 22 and the drain electrode 24. The semiconductor layer 20 contacts both the source electrode 22 and the drain electrode 24. The portion of the semiconductor layer that is positioned in the area between the source electrode and the drain electrode defines a channel.

Figure 3:
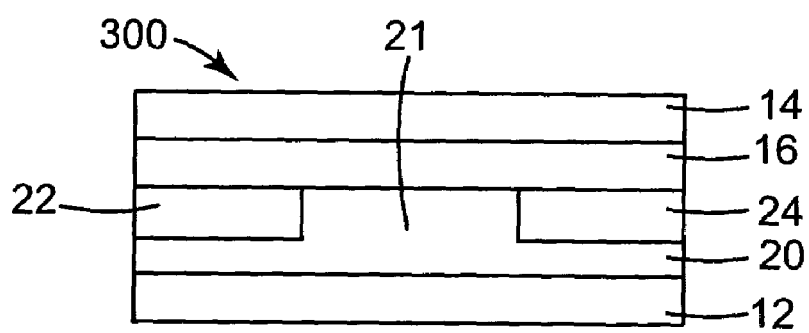
FIG. 3 is a schematic representation of a third exemplary thin film transistor.

The organic thin film transistor shown schematically in FIG. 3 can be prepared by providing a substrate 12; forming a semiconductor layer 20 adjacent to the substrate 12; positioning a source electrode 22 and a drain electrode 24 adjacent to the semiconductor layer 20 opposite the substrate 12 such that the source electrode 22 and drain electrodes 24 are separated from each other; depositing a gate dielectric layer 16 adjacent to the source electrode 22, the drain electrode 24, and a portion of the semiconducting layer 20 between the source electrode 22 and the drain electrode 24; and depositing a gate electrode 14 adjacent to the gate dielectric layer 16. Both the source electrode 22 and the drain electrode 24 contact the semiconductor layer 20. A portion of the semiconductor layer is positioned between the source electrode 22 and the drain electrode 24. This portion of the semiconductor layer defines a channel.

Another method of preparing an organic thin film transistor involves arranging multiple layers in the following order: a gate electrode; a gate dielectric layer; a semiconductor layer comprising a comprising a 6,13-bis(thienyl) pentacene compound of Formula I; and a layer having a source electrode and a drain electrode that are separated from each other, wherein the semiconductor layer contacts both the drain electrode and the source electrode. In some embodiments, a surface treatment layer can be positioned between the gate dielectric layer and the semiconductor layer. A substrate can be positioned adjacent to the gate electrode or adjacent to the layer containing the source electrode and the drain electrode. Exemplary organic thin film transistors according to this method are shown schematically in FIGS. 4 to 6.

The organic thin film transistor shown schematically in FIG. 4 can be prepared by providing a gate electrode 14; depositing a gate dielectric layer 16 adjacent to the gate electrode 14; forming a semiconductor layer 20 adjacent to the gate dielectric layer 16 (i.e., the gate dielectric layer 16 is positioned between the gate electrode 14 and the semiconducting layer 20); and positioning a source electrode 22 and a drain electrode 24 adjacent to the semiconductor layer 20. The source electrode 22 and the drain electrode 24 are separated from each other and both electrodes are in contact with the semiconductor layer 20. A portion of the semiconductor layer is positioned between the source and drain electrodes.

Figure 5:
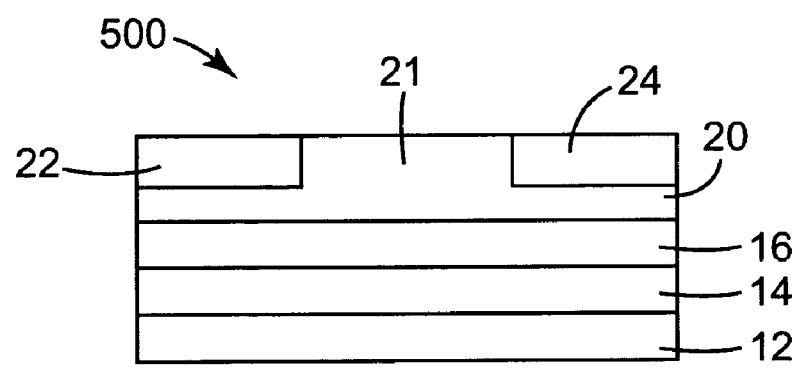
FIG. 5 is a schematic representation of a fifth exemplary thin film transistor.

The organic thin film transistor shown schematically in FIG. 5 can be prepared by providing a substrate 12, depositing a gate electrode 14 adjacent to the substrate 12, depositing a gate dielectric layer 16 adjacent to the gate electrode 14 such that the gate electrode 14 is positioned between the substrate 12 and the gate dielectric layer 16; forming a semiconductor layer 20 adjacent to the gate dielectric layer 16; and positioning a source electrode 22 and a drain electrode 24 adjacent to the semiconductor layer 20. The source electrode 22 and the drain electrode 24 are separated from each other and both electrodes are in contact with the semiconductor layer 20. A portion of the semiconductor layer 20 is positioned between the source electrode 22 and the drain electrode 24.

Figure 6:
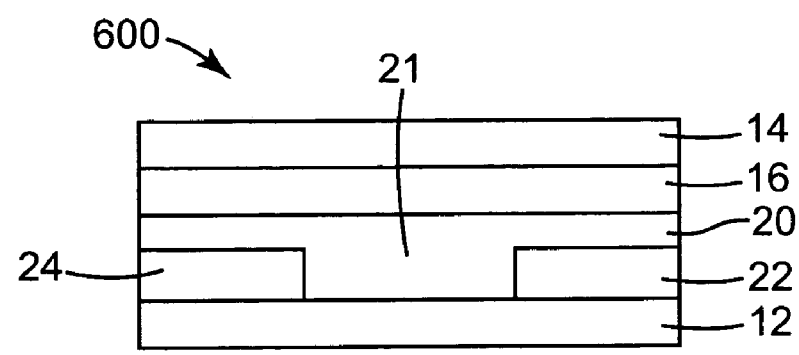
FIG. 6 is a schematic representation of a sixth exemplary thin film transistor.

The organic thin film transistor shown schematically in FIG. 6 can be prepared by providing a substrate 12; positioning a source electrode 22 and a drain electrode 24 adjacent to the substrate such that the source electrode 22 and the drain electrode 24 are separated from each other; forming a semiconductor layer 20 that contacts the source electrode 22 and the drain electrode 24; and depositing a gate dielectric layer 16 adjacent to the semiconductor layer opposite the source electrode 22 and the drain electrode 24; and depositing a gate electrode 14 adjacent to the gate dielectric layer 16. A portion of the semiconductor layer 20 is positioned between the source electrode 22 and the drain electrode 24.

The organic thin film transistors or other semiconductor devices such as integrated circuits can be prepared using flexible, repositionable polymeric aperture masks. The technique involves sequentially depositing material through a number of polymeric aperture masks formed with patterns that define layers, or portions of layers, of the semiconductor device. The use of such polymeric aperture masks are further described in U.S. Patent Publication Nos. 2003/0150384-A1 (Baude et al.), 2003/0152691-A1 (Baude et al.), and 2003/0151118-A1 (Baude et al.), incorporated herein by reference.

Repositionable polymeric aperture masks often have a thickness of 5 to 50 micrometers or 15 to 35 micrometers. The various deposition apertures in the aperture masks usually have widths less than 1000 micrometers, less than 50 micrometers, less than 20 micrometers, less than 10 micrometers, or even less than 5 micrometers. Apertures of these sizes are particularly useful in creating small circuit elements for integrated circuits. Moreover, one or more gaps between deposition apertures are typically less than 1000 micrometers, less than 50 micrometers, less than 20 micrometers, or less than 10 micrometers, which is also useful in creating small circuit elements. The aperture masks can have a pattern with a width greater than 1 centimeter, 25 centimeters, 100 centimeters, or even 500 centimeters. Patterns having these widths can be useful in creating various circuits over a larger surface area.

Various laser ablation techniques may be used to facilitate the creation of polymeric aperture masks having patterns of deposition apertures. In addition, stretching techniques and other techniques may be used to facilitate alignment of flexible polymeric aperture masks. Furthermore, methods of controlling sag in aperture masks may be used which can be particularly useful in using masks that include a pattern that extends over a large width.

Other methods known in the art can be used to prepare the semiconductor devices or the semiconductor layer. These methods include, for example, metal shadow masks; photolithography and/or etching; and printing methods such as inkjet, screen printing, gravure printing, and the like. In some embodiments, the semiconductor is cast as a layer from a solution.

In some methods that involve the use of aperture masks, semiconductor devices (e.g., integrated circuits) can be created solely using aperture mask deposition techniques, without requiring any of the etching or photolithography steps typically used to form such devices. The techniques can be particularly useful in creating circuit elements for electronic displays such as liquid crystal displays and low-cost integrated circuits such as radio frequency identification (RFID) circuits. In addition, such techniques can be advantageous in the fabrication of integrated circuits incorporating organic semiconductors, which typically are not compatible with photolithography or other wet chemical processes.

EXAMPLES

Objects and advantages of this invention are further illustrated by the following examples, but the particular materials and amounts thereof recited in these examples, as well as other conditions and details, should not be construed to unduly limit this invention.

All reagents were available from Aldrich Chemicals (Milwaukee, Wis.) unless otherwise noted.

2-Hexylthiophene was available from Alfa Aesar (Ward Hill, Mass.).

Preparatory Example 1

Preparation of pentacene-6,13-dione.

A solution of 62.7 grams (0.559 mmoles, 1.0 equivalents) of cyclohexan-1,4-dione and 150 grams of o-phthalaldehyde (1.12 mmoles, 2.0 equivalents) in 2000 mL of ethanol was heat to 28° C. To this solution was added 220 mL of a 1M aqueous solution of sodium hydroxide. The reaction temperature increased to 47° C. during the addition. The mixture was then heated at 40° C. for 4 hours. The mixture was cooled and a yellow solid precipitate was collected. The solid was stirred in 2000 mL of N,N-dimethylformamide and heated to 50° C. for 2 hours. The mixture was cooled to room temperature (i.e., 20° C. to 25° C.) and the yellow solid was collected and washed with N,N-dimethylformamide, then with acetone and dried to give 108.3 grams (62 mole percent yield) of a bright yellow solid.

Example 1

Preparation of 2-(13-thien-2-ylpentacene-6-yl)thiophene

A thiophene solution, prepared by dissolving thiophene (32.75 grams, 389.2 mmoles, 6 equivalents) in 800 mL of tetrahydrofuran (THF), was cooled to −70° C. and protected with an atmosphere of nitrogen. A 2.5 M (i.e., moles/liter) n-butyl lithium solution in hexanes (129.7 mL of solution, 324.3 mmoles of n-butyl lithium, 5 equivalents of n-butyl lithium) was added to the thiophene solution. The resulting mixture was stirred at −70° C. for 15 minutes, warmed to 31 23° C., and then held at −23° C. for 30 minutes. Hexanes (1320 grams) and then 6,13-pentacenedione (20.00 grams, 64.86 mmoles, 1 equivalent) were added to the mixture. The mixture was heated at 60° C. overnight. A stannous chloride solution, prepared by dissolving stannous chloride (63.99 grams, 337.5 mmoles, 5.203 equivalents) in hydrochloric acid (160 mL of a 10 weight percent hydrochloric acid), was added to the reaction mixture. The reaction mixture was heated for 2 hours at 60° C. and then cooled to room temperature (i.e., 20 to 25° C).

The aqueous phase was separated and discarded. The organic phase was dried over magnesium sulfate, filtered, and the filtrate was concentrated under a vacuum to give an oily blue solid. The solid was triturated with 5 volume percent dichloromethane in hexanes, then with 10 weight percent dichloromethane in hexanes, and finally with acetone. The solid was air dried to yield 12.7 grams (32 mole percent yield) of 2-(13-thien-2-ylpentacene-6-yl)thiophene. 1H NMR (400 MHz, THF-d8/TMS) δ 7.27 (d,d 3.1 Hz, 6.8 Hz 4H), 7.42 (d,d 1.1 Hz, 3.3 Hz 2H), 7.47 (d,d 3.3 Hz, 5.3 Hz, 2H), 7.80 (d,d 3.2 Hz, 6.5 Hz, 4H), 7.89 (d,d 1.2 Hz, 5.2 Hz 2H), 8.52 (s 4H).

Example 2

Preparation of 2-hexyl-5-[13-(5-hexylthien-2-yl) pentacene-6-yl]thiophene

A solution of 2-hexylthiophene, prepared by dissolving 2-hexylthiophene (12.50 grams, 148.5 mmoles, 6 equivalents) in 120 mL of THF, was cooled to −70° C. and protected with an atmosphere of nitrogen. A 2.5 M n-butyl lithium solution in hexanes (49.51 mL solution, 123.8 mmol n-butyl lithium, 5 equivalents n-butyl lithium) was added to the 2-hexylthiophene solution. The resulting mixture was stirred at −70° C. for 15 minutes, warmed to −23° C., and held at −23° C. for 30 minutes.

Hexanes (503.8 grams, 5846 mmoles, 236.1 equivalents) and then 6,13-pentacenedione (7.633 grams, 24.76 mmoles, 1 equivalent) were added to the mixture. The resulting mixture was heated at 60° C. overnight. Water (7.631 grams) and then a stannous chloride solution were added to the mixture. The stannous chloride solution was prepared by dissolving stannous chloride (24.42 grams, 128.8 mmoles, 5.203 equivalents) in hydrochloric acid (60 mL of 10 weight percent hydrochloric acid). The reaction mixture was heated for 2 hours at 60° C. and then cooled to room temperature.

The aqueous phase was separated and discarded. The organic phase was dried over magnesium sulfate, filtered, and the filtrate was concentrated under a vacuum to give an oily blue solid. This material was purified by column chromatography on silica gel.

1H NMR (400 MHz, THF-d8/TMS) δ 0.96 (t 7.0 Hz, 6H), 1.42 (m, 8H), 1.56 (quin 7.3 Hz, 4H), 1.89 (quin 7.6 Hz, 4H), 3.06 (t 7.6 Hz, 2H), 7.14 (d 3.2 Hz, 2H), 7.19 (d 3.3 Hz, 2H), 7.26 (d,d 3.0 Hz, 6.8 Hz, 4H), 7.80 (d,d 3.0 Hz, 6.6 Hz, 4H), 8.59 (s 4H).

Example 3

Preparation of trimethyl(5-{13-[5-(trimethylsilyl)thien-2-yl]pentacen-6-yl}thien-2-yl)silane A 2-trimethylsilylthiophene solution, prepared by dissolving 2-trimethylsilylthiophene (10.0 grams, 64.0 mmoles, 6 equivalents) in 26.2 mL THF, was cooled to −40° C. and protected with an atmosphere of nitrogen. A 2.6 M n-butyl lithium solution in hexanes (33.3 mL of solution, 53.3 mmol n-butyl lithium, 5 equivalents n-butyl lithium) was added to the 2-trimethylsilylthiophene. The resulting mixture was stirred for 30 minutes at a temperature between −50 and −30° C.

6,13-pentacenedione (3.29 grams, 10.7 mmoles, 1 equivalent) was added to the mixture. The mixture was stirred and allowed to slowly warm to room temperature overnight. The mixture was cooled to −5° C. and water (3.3mL) was added at −5° C. and then a stannous chloride solution in hydrochloric acid was added below 10° C. The stannous chloride was prepared by dissolving stannous chloride (10.1 grams, 53.3 mmoles, 5 equivalents) in a hydrochloric acid solution, which was prepared by adding 6.58 mL of a 12 M hydrochloric acid solution to 13.1 mL of water. The reaction mixture was stirred at room temperature overnight. The aqueous phase was separated and discarded. The organic phase was washed with water several times, and dried over magnesium sulfate and then filtered. The filtrate was concentrated under a vacuum. The residue was triturated with acetone and the solid was air dried to give 3.31 grams (53 mole percent yield).

1H NMR (400 MHz, THF-d8/TMS) δ 0.49 (s 18H), 7.26 (d,d 3.1 Hz, 6.8 Hz, 4H), 7.48 (d 3.3 Hz, 2H), 7.64 (d 3.3 Hz, 2H), 7.80 (d,d 3.2 Hz, 6.5 Hz, 4H), 8.51 (s 4H).

Example 4

Preparation of 5-[13-(2,2'-bithien-5-yl)pentacen-6-yl]-2,2'-bithiophene

A 2,2'-bithiophene solution was prepared by dissolving 2,2'-bithiophene (2.50 grams, 15.0 mmoles, 6 equivalents) in 100 mL THF and then cooled to −70° C. and protected with an atmosphere of nitrogen. A 2.5 M n-butyl lithium solution in hexanes (5.00 mL of solution, 12.5 mmoles of n-butyl lithium, 5 equivalents n-butyl lithium) was added over a period of 17 minutes. The mixture was stirred for 15 minutes at −65° C., warmed to −20° C., and then stirred at approximately −20° C. for 30 minutes with intermittent cooling. 6,13-pentacenedione (0.770 grams, 2.51 mmoles, 1.0 equivalent) was added and the mixture was heated to 60° C. overnight.

The mixture was cooled to room temperature (i.e., 20 to 25° C.) and diluted with 100 mL THF. Water (10 mL) and then a solution of stannous chloride were added slowly. The stannous chloride solution was prepared by dissolving stannous chloride (2.50 grams 13.0 mmoles, 5.2 equivalents) in hydrochloric acid, which was prepared by mixing 20 mL water and 10 mL concentrated hydrochloric acid. The reaction mixture was heated to 60° C. for 1.5 hours, cooled to 35° C., and diluted with 100 mL of water. The mixture was filtered to collect a blue solid. The solid was washed with acetone and air dried to give 0.50 grams (33 weight percent yield).

1H NMR (400 MHz, THF-d8/TMS) δ 7.11 (d,d 3.5 Hz, 5.1 Hz, 2H), 7.29 (d,d 3.1 Hz, 6.8 Hz, 4H), 7.35 (d 3.5 Hz, 2H), 7.40 (d,d 1.1 Hz, 3.5 Hz, 2H), 7.44 (d,d 1.1 Hz, 5.1 Hz, 2H), 7.61 (d 3.5 Hz, 2H), 7.89 (d,d 3.4 Hz, 6.6 Hz, 4H), 8.69 (s 4H).

Example 5

Preparation of 2-methyl-5-[13-(5-methylthien-2-yl)pentacen-6-yl]thiophene

A solution of 2-methylthiophene, prepared by dissolving 2-methylthiophene (10.0 grams, 102 mmoles, 6 equivalents) in 26.2 mL of THF, was cooled to −40° C. and protected with an atmosphere of nitrogen. A 1.6 M solution of n-butyl lithium in hexanes (53 mL of solution, 84.9 mmoles n-butyl lithium, 5 equivalents n-butyl lithium) was added. The mixture was stirred for 30 minutes at a temperature between −50 and −30° C. 6,13-Pentacenedione (5.23 grams, 16.9 mmoles, 1 equivalent) was added to this mixture. The resulting mixture was stirred and allowed to slowly warm to room temperature overnight (i.e., 20 to 25° C.).

The reaction mixture was cooled to approximately 15° C. while water (10 mL) and a hydrochloric acid solution were added. The hydrochloric acid solution was prepared by diluting 10.5 mL of 12 M hydrochloric acid (126 mmoles, 7.4 equivalents) with 20.9 mL of water. The mixture was stirred at room temperature for 1.5 hours. The aqueous phase was separated and the organic phase was washed with water and sodium bicarbonate. The organic layer was dried over magnesium sulfate and filtered. The filtrate was concentrated under a vacuum to give the product.

1H NMR (400 MHz, THF-d8/TMS) δ 2.70 (d, 1.1 Hz 6H), 7.11 (d,q 1.1 Hz, 3.3 Hz 2H), 7.17 (d 3.2 Hz, 2H), 7.25 (d,d 3.1 Hz, 6.8 Hz, 4H), 7.80 (d,d 3.3 Hz, 6.6 Hz, 4H), 8.62 (s 4H).

Example 6

Semiconductor devices using 2-(13-thien-2-ylpentacen-6-yl)thiophene

Test transistors were made on single crystal (i.e., <100>orientation), heavily doped, p-type silicon wafers that were obtained from Silicon Valley Microelectronics (San Jose, Calif.). A 1500 Å layer of sputtered alumina or a 1000 Å layer of high temperature thermal silicon oxide was formed on each wafer front using evaporative vapor deposition. A 5000 Å layer of aluminum metal was vapor deposited onto the backside of each wafer. In this configuration, the doped wafer capped with aluminum served as the gate electrode and the alumina or silicon oxide functioned as the gate dielectric when organic thin film transistors (OTFTs) were prepared.

For a polymeric surface-treated sample, the poly(a-methylstyrene) (AMS) coating was applied by spin coating (300 rpm/5 sec, then 2000 rpm/15 sec) a toluene solution of the polymer onto the sample having alumina as the gate dielectric. The surface-treated sample was heated in an oven for 30 minutes at 110° C.

The semiconductor, 6,13-dithien-2-yl)pentacene was deposited by vacuum sublimation ($10^{-6}$ Torr) onto the substrates at a rate of 0.3 Å/sec to reach a thickness of 600 Å (60 nm) as measured using a quartz crystal microbalance. Gold source and drain electrodes were evaporated through a shadow masked onto the semiconductor layer. The devices had a channel length of 60 to 100 μm and a channel width of 1000 μm.

Transistor performance was tested at room temperature in air using techniques known in the art. A Semiconductor Parameter Analyzer (Model 4145A from Hewlett-Packard, Palo Alto, Calif.) was used for the testing. The square root of the drain current ($I_d$) was plotted as a function of gate-source bias ($V_g$), from +10 to −40 V for a constant source-drain bias ($D_{VD}$) of −40 V. The saturation field effect mobility was calculated from the linear portion of the curve using the specific capacitance of the gate dielectric, the channel width and the channel length. The x-axis extrapolation of this straight-line fit was taken as the threshold voltage ($V_t$). In addition, plotting $I_d$ as a function of $V_{gy}$ yielded a curve where a straight line fit was drawn along a portion of the curve containing $V_t$. The inverse of the slope of this line was the sub-threshold slope (S). The on/off ratio was taken as the difference between the minimum and maximum drain current ($I_d$) values of the $I_d$-$V_g$ curve. Table I displays the results of the various devices.

TABLE I

Thin Film Transistor Performance Test Data

| Dielectric Treatment/Surface Treatment | Mobility (cm²/V-sec) | On/Off Ratio | $V_t$ (volts) | S V/decade |
|---|---|---|---|---|
| Alumina | $3.45 \times 10^{-4}$ | $1.5 \times 10^3$ | −18.2 | 2.06 |
| Silica | $6.92 \times 10^{-6}$ | 80.4 | 0.0429 | 5.01 |
| Alumina/ α-methylstyrene | $1.83 \times 10^{-2}$ | $1.1 \times 10^4$ | −3.38 | 1.04 |

Example 7

Solubility of pentacene derivatives.

The solubility of each compound prepared in Examples 1 to 4 was determined by the following method. The proton NMR spectra of saturated solutions of the compounds prepared in Examples 1 to 4 dissolved in tetrahydrofuran-$d_8$ were compared with the proton NMR spectrum of a standard solution (i.e., known concentration) of the compound of Example 2, which was 2-hexyl-5-[ 13-(5-hexylthien-2-yl)pentacene-6-yl]thiophene, dissolved in tetrahydrofuran-$d_8$. The same lot of tetrahydrofuran-$d_8$ was used to make all of the solutions. The standard solution was prepared by dissolving 7.0 mg of the compound of Example 2 in 936 mg of tetrahydrofuran-$d_8$ to give a 0.742 weight percent solution. Saturated solutions of the compounds of Examples 1 to 4 were prepared by placing an excess of the corresponding compound in approximately 1 mL of tetrahydrofuran-$d_8$ and mixing for 30 minutes. The solutions were filtered and placed in an NMR tube and the corresponding proton NMR spectra were obtained.

For the standard (0.742 weight percent solution of the compound of Example 2), the NMR integration for the absorption at 8.59 ppm (the most down-field absorption corresponding to the four protons at positions 5, 7, 12 and 14) was compared to the absorption of the residual protio-tetrahydrofuran at 3.6 ppm to give a relative ratio of moles of the compound of Example 2 to moles of protio-tetrahydrofuran of 0.33. The molar ratio of the compound of Example 2 to tetrahydrofuran (protio- and deutero-) in the standard solution is $8.83 \times 10^{-4}$. This molar ratio ($8.83 \times 10^{-4}$) divided by the relative ratio of moles of the compound of Example 2 to moles of protio-tetrahydrofuran (0.33) gave a factor of $2.68 \times 10^{-3}$. Multiplying this factor by the proton NMR integration for the saturated solutions of the corresponding compounds of Example 1 to 4 gave the ratio of moles of pentacene derivative to moles of tetrahydrofuran in the saturated solutions. This allowed the calculation of the concentrations for the various solutions of compounds of Examples 1 to 4 as shown in the table below.

TABLE 2

Solubility of Examples 1 to 4

| Compound | ppm H1 adsorption | Moles of compound/ moles of protio-THF | Moles of compound/ moles of THF | Molecular weight | Weight percent in THF | Molarity in THF |
|---|---|---|---|---|---|---|
| Example 1 | 8.52 | 0.2 | $5.35 \times 10^{-4}$ | 442.61 | 0.327 | $6.58 \times 10^{-3}$ |
| Example 2 | 8.59 | 4.02 | $1.08 \times 10^{-2}$ | 610.93 | 8.35 | $1.22 \times 10^{-1}$ |
| Example 3 | 8.51 | 1.1 | $2.94 \times 10^{-3}$ | 586.97 | 2.34 | $3.54 \times 10^{-2}$ |
| Example 4 | 8.69 | 0.06 | $1.61 \times 10^{-4}$ | 606.86 | 0.135 | $1.98 \times 10^{-3}$ |

Example 8

Stability in tetrahydrofuran

The solution stabilities of the compounds of Examples 1 to 4 were determined by proton NMR analysis of saturated solutions of the corresponding compounds in tetrahydrofuran-$d_8$. Comparing the proton NMR integration of the four protons at positions 5, 7, 12 and 14 (8.51 ppm to 8.69 ppm) to the integration of the four corresponding protons from the endoperoxide (the major and only detectable decomposition product, 7.93 ppm to 7.98 ppm), the percent increase of this impurity was determined for each compound. The solutions were prepared by dissolving the corresponding compound in tetrahydrofuran-$d_8$ and the proton NMR spectra were obtained to determine the initial concentration of endoperoxide for each sample. The solutions were allowed to stand protected from light at room temperature (i.e., 20° C. to 25° C.) for 120 hours. Proton NMR spectra of the aged samples were taken and the increase in absorption of the endoperoxide was used to calculate the data shown in Table 3. The formation of the endoperoxide is shown in the following reaction for compounds of Formula II.

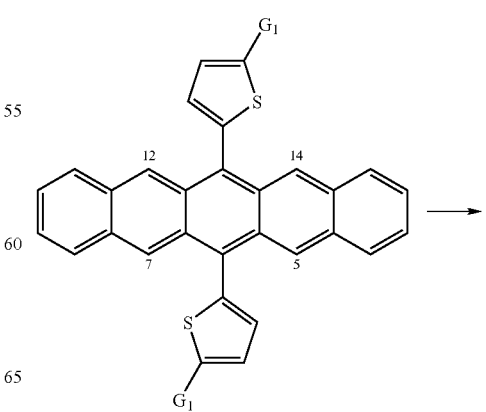

-continued

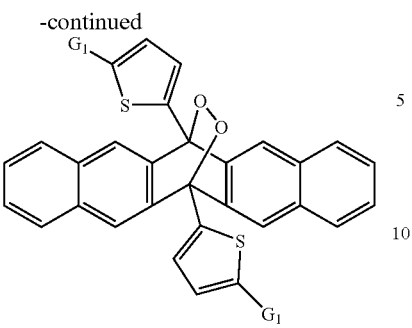

TABLE 3

| | Stability in Tetrahydrofuran | | | | | | |
|---|---|---|---|---|---|---|---|
| Compound | ppm of H1 adsorption for compound | ppm of H1 adsorption for impurity | NMR integration— initial | Mole percent impurity— initial | NMR integration— 120 hours | Mole percent impurity— 120 hours | Mole percent increase |
| Example 1 | 8.52 | 7.85 | 0.06 | 5.66 | 0.27 | 21.26 | 15.60 |
| Example 2 | 8.59 | 7.89 | 0.03 | 2.91 | 0.12 | 10.71 | 7.80 |
| Example 3 | 8.51 | 7.83 | 0.02 | 1.96 | 0.05 | 4.76 | 2.80 |
| Example 4 | 8.69 | 7.98 | 0.03 | 2.91 | 0.07 | 6.54 | 3.63 |

We claim:

1. A 6,13-bis(thienyl)pentacene compound of Formula I:

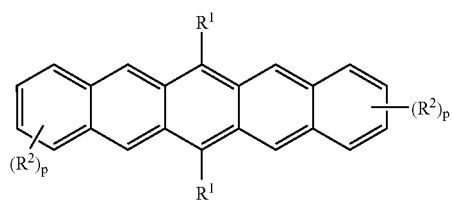

wherein each $R^1$ is independently a thienyl group that is substituted with an alkenyl, alkynyl, halo, haloalkyl, trialkylsilyl, thienyl, or combination thereof;

each $R^2$ group is independently an alkoxy, alkyl, alkenyl, alkynyl, amino, halo, haloalkyl, hydroxy, or two $R^2$ groups taken together form a ring having 5 to 7 ring members, the ring being carbocyclic or heterocyclic and saturated or unsaturated; and each p is independently an integer of 0 to 4.

2. The compound of claim 1, wherein p is equal to 0.

3. The compounds of claim 1, wherein p is equal to 0 and each $R^1$ is independently a thienyl substituted with an alkenyl, alkynyl, trialkylsilyl, or thienyl.

4. The compound of claim 1, wherein the 6,13-bis(thienyl)pentacene compound is a compound of Formula II:

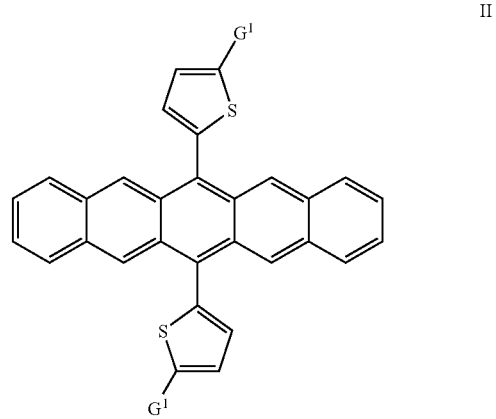

wherein $G^1$ is independently alkenyl, alkynyl, halo, haloalkyl, trialkylsilyl, thienyl, or a combination thereof.

* * * * *

UNITED STATES PATENT AND TRADEMARK OFFICE
CERTIFICATE OF CORRECTION

PATENT NO. : 7,319,153 B2
APPLICATION NO. : 11/192950
DATED : January 15, 2008
INVENTOR(S) : Dennis E. Vogel It is certified that error appears in the above-identified patent and that said Letters Patent is hereby corrected as shown below:

Column 7, Line 32 (Approx.) - Delete "cyclohexan-1" and insert -- cyclohexane-1 --, therefor.

Column 15, Line 56 - Delete "cyclohexan-1" and insert -- cyclohexane-1 --, therefor.

Column 16, Line 13-14 (Approx.) - Delete "31 23°C.," and insert -- -23°C., --, therefor.

Column 17, Line 4 (Approx.) - Delete "pentacen-" and insert -- pentacene- --, therefor.

Column 17, Line 38 (Approx.) - Delete "pentacen-" and insert -- pentacene- --, therefor.

Column 18, Line 25 - Delete "(d,q" and insert -- (d,d --, therefor.

Column 18, Line 48 (Approx.) - Before "6,13" insert -- ( --.

Column 18, Line 67 - Delete "$V_{gyielded}$" and insert -- $V_g$ yielded --, therefor.

Column 19, Line 44 (Approx.) - Delete "[ 13" and insert -- [13 --, therefor. (Consider Space)

Column 22, Line 63 (Approx.) - Before "$G^1$" insert -- each --.

Signed and Sealed this

First Day of July, 2008

JON W. DUDAS
*Director of the United States Patent and Trademark Office*